United States Patent [19]

Holmes et al.

[11] 4,318,723
[45] Mar. 9, 1982

[54] CRYOGENIC DISTILLATIVE SEPARATION OF ACID GASES FROM METHANE

[75] Inventors: Arthur S. Holmes, Shrewsbury; James M. Ryan, Weston, both of Mass.

[73] Assignee: Koch Process Systems, Inc., Westborough, Mass.

[21] Appl. No.: 94,226

[22] Filed: Nov. 14, 1979

[51] Int. Cl.³ .............................................. F25J 3/02
[52] U.S. Cl. ................................. 62/20; 62/28; 62/40; 62/24
[58] Field of Search ............................ 62/24–28, 62/17, 20

[56] References Cited

U.S. PATENT DOCUMENTS

| | | | |
|---|---|---|---|
| 2,573,341 | 10/1951 | Kniel | 62/28 |
| 3,595,782 | 7/1971 | Bucklin et al. | 62/27 |
| 3,899,312 | 8/1970 | Kruis et al. | 62/20 |
| 3,977,203 | 8/1976 | Hinton et al. | 62/20 |
| 4,149,864 | 4/1979 | Eakman et al. | 62/28 |
| 4,185,978 | 1/1980 | McGalliard | 62/28 |

*Primary Examiner*—Norman Yudkoff
*Attorney, Agent, or Firm*—Hamilton, Brook, Smith and Reynolds

[57] ABSTRACT

A method of eliminating solids formation in a cryogenic distillative separation of acid gases from methane is disclosed. This method comprises adding a solids-preventing agent to the solids potential zone of the distillation column. Typical solids-preventing agents are one or more $C_2$–$C_5$ alkanes, or other nonpolar liquids which are miscible with methane at the column conditions. The elimination of solids formation permits a more complete separation to be achieved.

20 Claims, 9 Drawing Figures

CRYOGENIC DISTILLATIVE SEPARATION OF ACID GASES FROM METHANE

DESCRIPTION

1. Technical Field

This invention is in the field of cryogenic distillation.

2. Background Art

It is often desirable to separate acid gases, such as carbon dioxide ($CO_2$), from gas mixtures containing methane in sufficient amounts to make methane recovery commercially feasible. Gas streams obtained from natural gas wells, for example, often contain relatively high amounts of carbon dioxide, which lowers the heating value of the gas, is highly corrosive, and causes the gas to be commercially unacceptable. In such situations, carbon dioxide must be removed from the gas stream in order to meet the carbon dioxide specification for salable gas product.

There are, of course, many other applications in which it is advantageous or necessary to remove carbon dioxide from methane-containing gas mixtures. For example, carbon dioxide usually must be separated from gas mixtures caused by injecting carbon dioxide-containing gases into oil wells for enhanced oil recovery. Similar separations are often desirable in coal gasification and petrochemical plants. Further, it is sometimes necessary to separate carbon dioxide from hydrogen-rich gas mixtures, such as synthesis gas used for ammonia production.

Because of the frequent need for carbon dioxide removal or separation from such gas streams, much work has been devoted to developing processes for methane/carbon dioxide separations. Generally, the processes developed can be classified into three categories, which are $CO_2$ adsorption by solids, $CO_2$ absorption by chemical solvents and $CO_2$ absorption by physical solvents.

Adsorption by solids has generally been economically practical, however, only when the feed gas contained relatively small amounts of carbon dioxide and it was required that substantially all of the carbon dioxide be removed. Thus, adsorption processes have limitations in their application.

Chemical absorption systems have generally employed solvents, including amines, such as monoethanolamine and diethanolamine, or carbonates, such as potassium carbonate. Physical absorption systems have employed polar liquid solvents, such as methanol, ethylene glycol, dimethylether, polyethylene glycol, methylpyrrolidone and propylene carbonate. In general, chemical and physical absorption systems have suffered a number of economic disadvantages in separations where the feed stream contained high amounts of carbon dioxide. Such disadvantages include relatively high utility consumption, high maintenance costs due to the corrosive nature of the solvents, and degradation of the solvents by the products separated.

The desirability of a cryogenic distillative separation for a methane/carbon dioxide gas mixture has been recognized, and the relative volatility of methane to carbon dioxide is reasonably high which makes such a distillative separation possible. Nevertheless, the behavior of a methane/carbon dioxide system has prevented such a distillative separation from becoming commercially practical for separations requiring substantially complete $CO_2$ separation from high-carbon dioxide content gases. This is because solid carbon dioxide coexists with a vapor and liquid mixture of methane and carbon dioxide at certain compositions, temperatures and pressures encountered in distillative separations. At these conditions, carbon dioxide freezes out of solution and would potentially plug up a distillation column as well as other equipment thereby making the process inoperative. On the other hand, at higher pressures, where carbon dioxide does not freeze out, methane-rich mixtures become supercritical fluids not subject to further purification of methane by distillation. Thus, raising the pressure in a column above that where carbon dioxide freeze-out occurs is not usually a viable alternative to achieving further methane separation.

Because of this behavior of the methane/carbon dioxide system, efforts to employ a cryogenic distillative separation have employed special precautions to avoid conditions in the distillation column or columns where carbon dioxide freeze-out occurs. In some cases, pre-separation techniques have been employed to reduce the carbon dioxide content of a gas stream to a point below that at which freeze-out occurs prior to introducing the gas stream to the column. An example of such a process is disclosed in Streich, U.S. Pat. No. 3,683,634, which describes the pretreatment of a gas stream to reduce the amount of carbon dioxide therein prior to introducing the gas stream into a low pressure distillation column. Although the feed gas described contains only about 1% carbon dioxide, it is first treated to remove most of the carbon dioxide before the gas stream is introduced into the low pressure column. Because of the diluted carbon dioxide content, the distillation column does not contain a zone of operation where conditions are such that carbon dioxide freeze-out occurs.

Another process involving distillative separation of a gas mixture in which the carbon dioxide content is initially low, but even further diluted prior to introduction to a low pressure column, is disclosed in Pachaly, U.S. Pat. No. 3,724,226.

Other distillative approaches have been described in which the feed to a distillation column contained a high content of carbon dioxide, and in such approaches, it was necessary to operate the column at conditions of temperature, pressure and composition to avoid the zone of solids formation in the distillative process. Unfortunately, such conditions also limit the extent of the separation which can be achieved. Several such processes are described in the patent literature, including: the process for separating a gaseous mixture containing 30–90 mole percent carbon dioxide described in Trentham et al., U.S. Pat. No. 4,152,129; the process for separating carbon dioxide and other acid gas components in a column operated at high pressure and low temperature from a gaseous mixture containing hydrocarbons and hydrogen in Eakman et al., U.S. Pat. No. 4,149,864; the process for producing an ethane and heavier hydrocarbon product having low carbon dioxide content from high content (e.g., 1–10%, by volume) feed gas described in Bucklin et al., U.S. Pat. No. 3,595,782; and the method for separation of ethylene or ethane from a mixture of gases also containing methane and hydrogen described in Koble, U.S. Pat. No. 2,775,103.

Harmens in U.S. Pat. No. 3,306,057 describes yet another process in which feed gas is reduced to about 11% carbon dioxide in the overhead production of a distillation column. Further carbon dioxide separation is achieved in a heat absorber containing a slurry of solid carbon dioxide in a carrier liquid. Thus, the composition where carbon dioxide freeze-out is really a problem is intentionally avoided in the distillation column and handled in a separate and external slurry processing heat exchanger.

Another approach to separating methane/carbon dioxide gas mixtures involves the use of both a low pressure column and a high pressure column to avoid creating the conditions where carbon dioxide freeze-out occurs. See French Pat. No. 2,312,001; and Schianni, G. C., paper presented at Natural Gas Processing and Utilisation Conference, Proceedings Vol. 1, Institution of Chemical Engineers Symposium Series 44, 50–55 (1976).

Despite a large amount of research and development which has been directed to finding a commercially viable cryogenic distillative separation for removing carbon dioxide and other acid gas components from methane, particularly in one column, none has been developed to date which is entirely satisfactory.

DISCLOSURE OF THE INVENTION

This invention relates to the separation of methane from a gas mixture containing methane and one or more acid gas components, such as carbon dioxide, by an improved cryogenic distillative separation. This process is effective for feed gas mixtures which contain relatively high percentages of acid gas components, such as a feed gas mixture containing high carbon dioxide content. Of course, the method described is capable of handling feed gases containing low carbon dioxide content and/or additional components besides methane and carbon dioxide. Typical additional components include nitrogen and hydrocarbons of higher molecular weight than methane.

In this process, a distillation column is used to separate feed gas into an overhead product which is substantially free of acid gas components and a bottoms product substantially free of methane. Unlike other prior distillative separations, the distillation column is operated at temperatures, compositions and pressures which produce a solids potential zone for acid gas components within the tower. Such conditions are necessary, in fact, to separate a high $CO_2$-content gas if the overhead product gas stream is to contain very low amounts of carbon dioxide.

The term "solids potential zone" is employed because, as explained below, although conditions in the tower are such that acid gas solids would normally occur, thus interfering with the desired separation, the process described herein prevents actual solids formation from occurring.

In order to avoid actual acid gas solids formation in the solids potential zone, an agent for preventing acid gas solids is added to the column so that it is present throughout the solids potential zone. This agent can be an external additive, or in the alternative, can be one or more recycled components from the bottoms product taken from the distillation column. The solids-preventing agent is added in a sufficient quantity to prevent carbon dioxide or other acid gas components from forming solids in the solids potential zone of the column, thereby allowing a more complete distillative separation of methane from acid gas components to be achieved.

The cryogenic distillative separation described herein offers significant advantages over prior distillative processes operated to avoid conditions where acid gas solids occurred, as well as advantages over physical and chemical absorption systems. A major advantage, for example, is that a more complete distillative separation of methane from acid gas components is possible in one column. This is in contrast to prior separations requiring a multi-column system or a system having one or more distillation columns together with preseparation apparatus to remove most of the acid gas components prior to admitting the feed gas to the column.

The addition of certain solids-preventing agents also raises the critical pressure and temperature of the system thereby allowing more efficient and/or economical separations to be performed.

The distillative separation described herein is also cost effective, particularly for high-carbon dioxide feed streams. In fact, less energy is required to be supplied for high carbon dioxide content gases with this method than with many of the prior art absorption processes. Capital investment can also be lower since additional columns or carbon dioxide preseparation apparatus is not required.

Further, a potential by-product of subsequent bottoms product separation from a feed containing methane and carbon dioxide is high-purity pressurized carbon dioxide. This pressurized high-purity product is not provided with many of the competing separation processes commercially available, such as chemical or physical absorption.

Natural gas liquids (NGL) are another by-product which can be conveniently achieved with this cryogenic distillative separation if they are present in the feed. Thus, the separation of methane from carbon dioxide and NGL can be conveniently carried out in one distillation column employing this invention.

BEST MODE OF CARRYING OUT THE INVENTION

This invention will now be described in more specific detail with regard to the figures.

The difficulty in performing a cryogenic distillative separation of the methane/carbon dioxide binary system can be illustrated in two ways. One of these employs FIG. 1, which is a vapor-liquid-solid phase diagram for the methane/carbon dioxide binary system at 650 psia. For purposes of simplifying the diagram, actual data points for the binary system are not shown, but the data employed to make the plot were based upon data taken from Donnelly, H. G. and Katz, D. L., *Ind. Eng. Chem.*, 46, 511 (1954). As can be seen, the methane/carbon dioxide binary system at 650 psia contains areas of liquid only, vapor only, vapor and liquid in coexistence and areas in which solids coexist with either liquor or vapor. The solids are caused by freeze-out of carbon dioxide at certain conditions. Experimental data from other sources indicate that solid carbon dioxide formation occurs over a broader range of conditions than shown in FIG. 1, which would be even more disadvantageous in an attempted cryogenic distillative separation.

Figure 1:
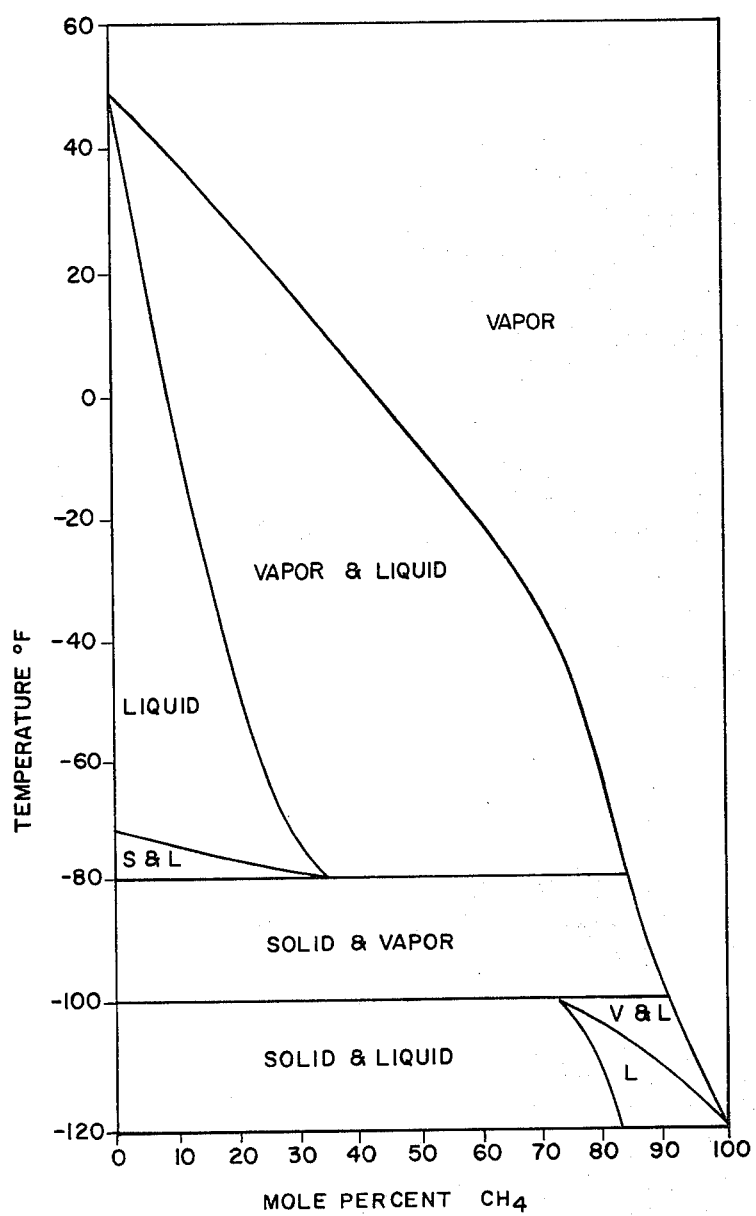
FIG. 1 is the vapor-liquid-solid phase diagram for the methane/carbon dioxide binary system at 650 psia.

As can be seen, there is a solids formation area of the phase diagram presented in FIG. 1 which would be encountered in a distillation column operating at 650 psia if it was desired to separate a binary mixture of methane and carbon dioxide into a highly pure methane overhead product. This can be illustrated if it is assumed that it is desired to separate a feed of 50% carbon dioxide/50% methane at 60° F. into a methane product having 1% carbon dioxide. As this feed is chilled, it reaches the zone of vapor and liquid at a temperature of about −8° F. At −40° F., the system has a vapor containing about 72% methane and a liquid in equilibrium with the vapor and which contains about 18% methane. Further cooling increases the percent methane in the vapor, until at about −80° F. the upper limit of about 85% methane in the vapor is reached without solids present. Any further cooling would produce carbon dioxide solids which would interfere with operation of the distillation tower. Thus, it can be seen that it is possible to achieve a product having about 85% methane, but no more, with one distillation column operating at 650 psia because of the properties of a methane/carbon dioxide binary system.

The presence of a solids-formation zone has severely limited the use of cryogenic distillative separations for methane/carbon dioxide systems, as previously described, to those employing preseparation techniques to dramatically lower the carbon dioxide level of feed gas to the distillation column or the operation of the column at conditions which avoid creation of a solids potential zone therein. The latter techniques usually place severe restrictions on the purity of the overhead product which can be obtained.

It can be seen from FIG. 1 that feed streams already low in carbon dioxide, e.g., less than about 9% can be further separated in a system at 650 psia without encountering solids formation. Thus, it is the feeds which are relatively high in carbon dioxide and which need to be separated into methane products having most of the carbon dioxide removed which present the problems.

Figure 2:
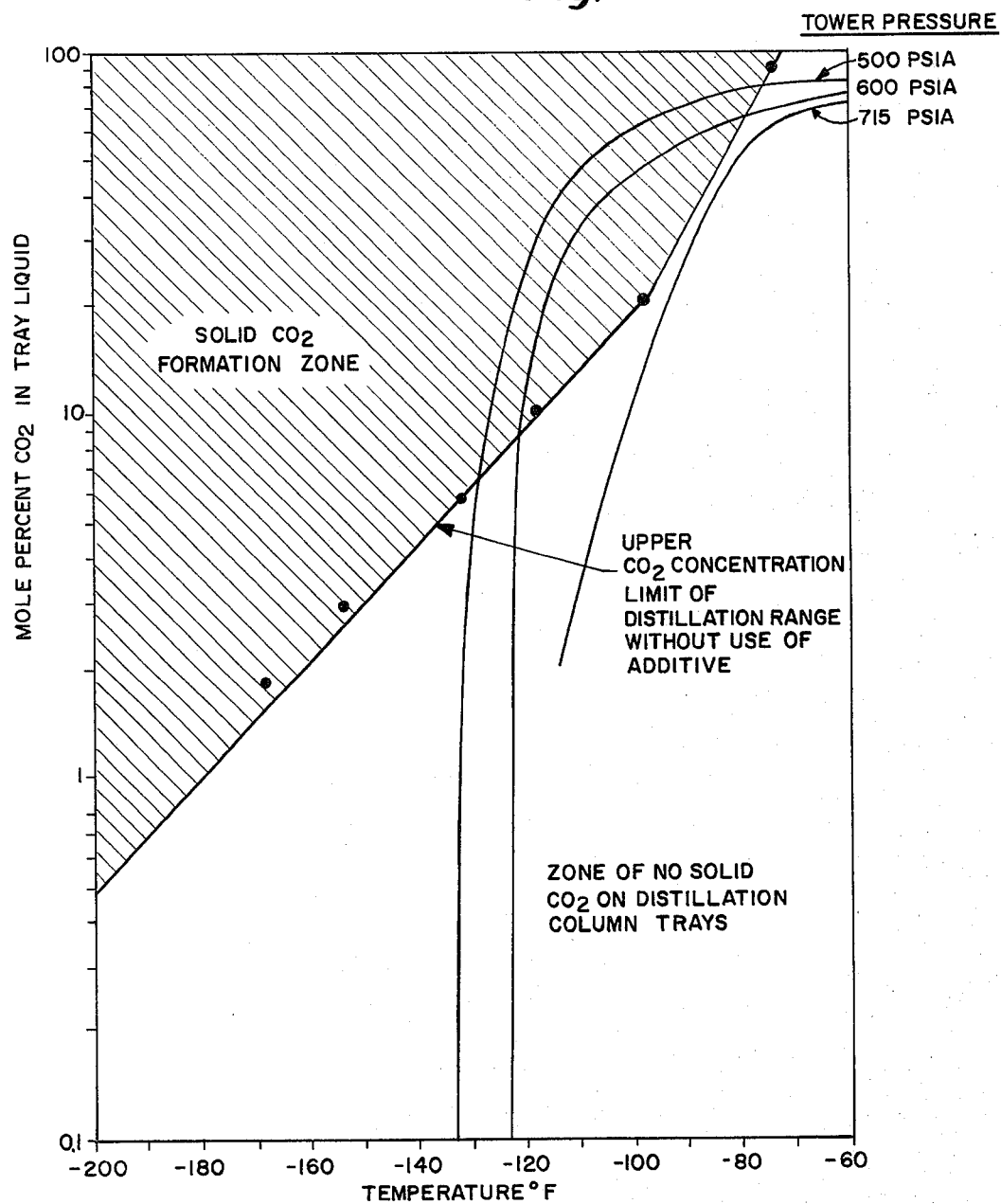
FIG. 2 is a plot illustrating tray liquid compositions in the distillation of a carbon dioxide/methane binary at three column pressures and the zone of solid $CO_2$ formation.

FIG. 2 illustrates the problems encountered in attempting to obtain substantially complete separations of carbon dioxide from methane by a cryogenic distillation in one tower from another perspective. FIG. 2 is a plot of liquid compositions present on trays in a distillative separation of a binary methane/carbon dioxide feed in columns operated at 500, 600 and 715 psia. The solids potential zone for carbon dioxide is the area to the left of the line representing the carbon dioxide solubility limits in the pure binary system. Solubility data are from Cheung, H. and Zander, E. H., *CEP Symposium Series* No. 88, Vol. 64 (1968) and Kurata, F., *AIChE J.* Vol. 8, No. 4, (1964). The 500 and 600 psia data were obtained from computer simulations using a plate-to-plate column calculation program named the PROCESS$^{SM}$ Simulation Program, June–July 1979, which is available from Simulation Sciences, Inc., Fullerton, Cal. The 715 psia data were taken directly from Trentham et al., U.S. Pat. No. 4,152,129.

As can be seen from FIG. 2, at 500 psia a carbon dioxide solids zone exists between liquids containing about 6–7% carbon dioxide to about 80% carbon dioxide. Similarly, at 600 psia, the range is from about 9% to about 65% carbon dioxide. Since liquid compositions within both of these ranges are present in a cryogenic distillative separation of a binary of 50% carbon dioxide/50% methane, solids will be encountered. Once through the solids formation zone, very complete separations are possible. Once again, it can be seen that the problem of solids formation is not present if the liquid composition is relatively low in carbon dioxide, i.e., below about 6–7% at 500 psia and below about 9% at 600 psia.

FIG. 2 also indicates that the 715 psia line misses the solids formation zone. Such a high pressure, however, approaches critical pressure of the mixture at the column top which limits the separation which can be achieved and makes design and/or operation of a distillation tower difficult and impractical.

Figure 3:
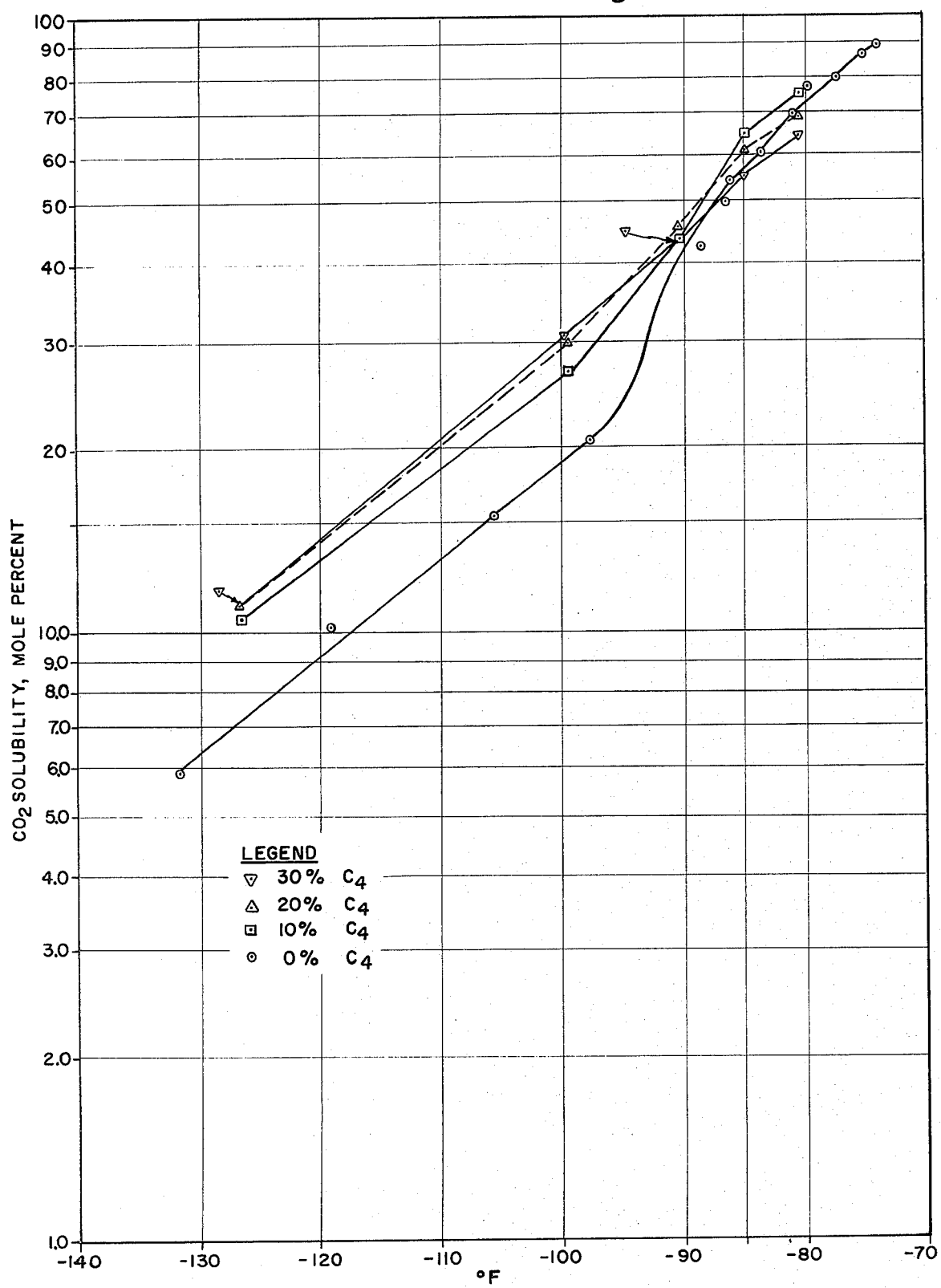
FIG. 3 is a plot of carbon dioxide solubility at various temperatures in liquid methane and liquid mixtures of methane and n-butane at conditions of vapor-liquid-solid equilibria.

FIG. 3 is a plot of data illustrating the solubility of carbon dioxide at various temperatures in pure methane and in methane-butane mixtures containing 10%, 20% and 30% butane, respectively. The liquid phase has the indicated percent butane and the percent carbon dioxide is indicated on the ordinate. The balance is methane. The helpful effect of adding butane, one preferred solids-preventing agent, is illustrated. As can be seen, the addition of butane substantially increases the solubility of carbon dioxide and decreases the freezing temperature. As indicated, as much as 10°–15° F. extra latitude can be gained by the addition of butane.

Figure 4:
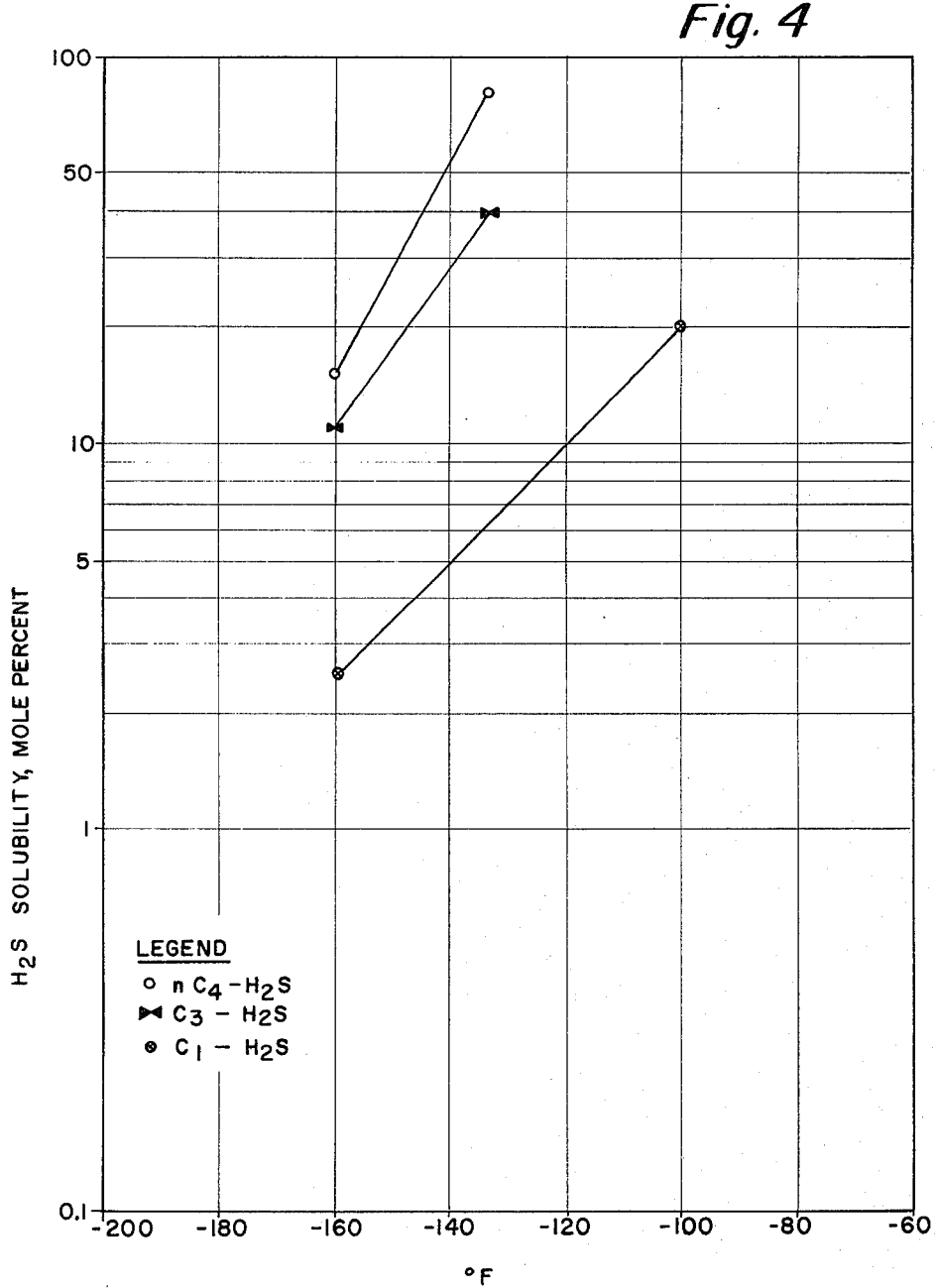
FIG. 4 is a plot of hydrogen sulfide solubility in liquid binary systems with each of liquid methane, liquid propane and liquid butane.

FIG. 4 is a plot of data illustrating the solubility of hydrogen sulfide, another acid gas, at various temperatures in binary mixtures of hydrogen sulfide and each of the light hydrocarbons, methane, propane and n-butane. As can be seen, the solubility of $H_2S$ is significantly larger in propane and butane than in methane.

Figure 5:
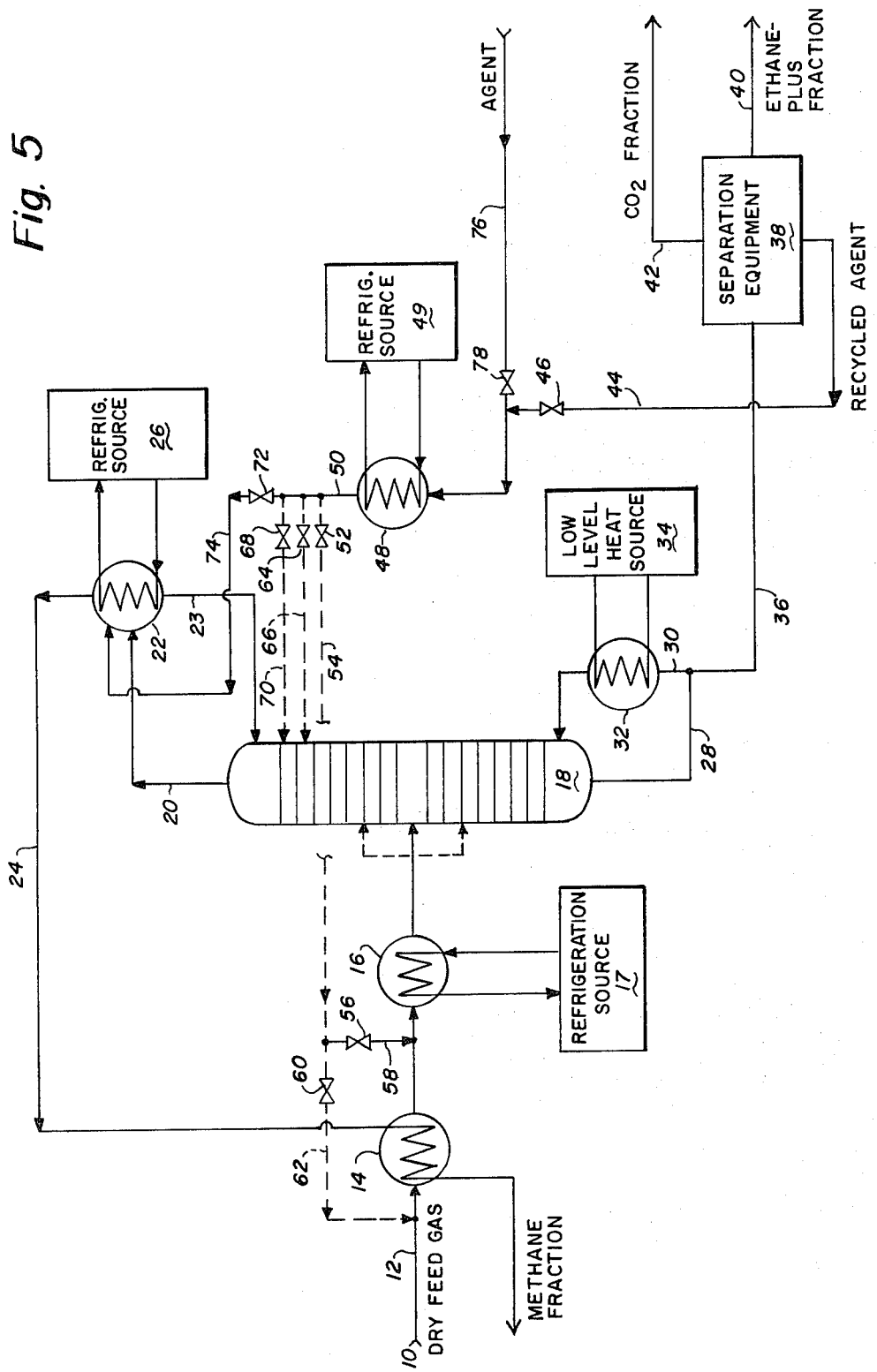
FIG. 5 is a schematic flow diagram illustrating apparatus suitable for carrying out the invention described herein; and, FIGS. 6–9 are plots of computer generated data illustrating tray liquid compositions in the distillation of a carbon dioxide/methane binary and the effects of varying amounts of solids-preventing agent as well as the effects of different points of addition for various tower conditions.

An apparatus for carrying out a separation of methane from carbon dioxide according to this invention is schematically illustrated in FIG. 5. Dry feed gas 10, containing a mixture of methane and carbon dioxide, and usually other components such as nitrogen and higher alkanes, enters in inlet feed line 12. The feed gas is initially cooled in pre-cooler 14 and subsequently cooled to cryogenic temperatures in heat exchanger 16 which receives refrigeration from refrigeration source 17. Although not essential, it is typical to cool dry feed gas 10 in exchanger 16 to a temperature sufficiently low to liquify a portion thereof. Thereafter, cryogenically cooled feed is introduced onto one or more of the trays in distillation column 18. Distillation column 18 contains a number of vapor-liquid contact devices, such as trays or packing, with the exact number of contact stages depending upon the required operating conditions, of course. Purified methane is withdrawn in overhead line 20 and passed through partial condenser 22. Product methane is withdrawn in line 24 and passes through precooler 14. Condenser 22 receives refrigeration from refrigeration source 26 and provides reflux in line 23 to tower 18. In some systems, of course, a condenser is not employed.

Bottoms product exits from column 18 through line 28 and part of the bottoms product is recycled to column 18 via line 30 which passes through reboiler heat exchanger 32 supplied with heat energy from low level heat source 34. This provides vaporization heat to the bottom of column 18. The balance of the bottoms product passes through line 36 to further separation equipment 38 for separating out other fractions, such as an ethane plus fraction separated and collected through line 40. A carbon dioxide fraction is extracted through line 42.

It is also possible to separate solids-preventing agent from the bottoms product in many cases, such as natural gas liquids (NGL), which is shown as being recycled to the column. The recycled solids-preventing agent exits from the separation equipment 38 in line 44 and valve 46 regulates the flow of such recycled agent through exchanger 48, cooled by refrigeration source 49, back to column 18. Recycled, cooled solids-preventing agent exiting from heat exchanger 48 flows in line 50 and can then be directed to a number of possible entry points to column 18.

For example, recycled solids-preventing agent can be directed through flow control valve 52 into line 54 and added to dry feed gas 10 via valve 56 in line 58 at a point immediately prior to exchanger 16, or through flow control valve 60 and line 62 at a point prior to precooler 14. In some cases where there is a problem with potential solids formation at the point in which dry feed gas 10 enters the column, such recycled agent is desirable.

Alternatively, recycled solids-preventing agent in line 50 can be directed through flow control valve 64 and line 66 to an elevated point in column 18. A still further alternative is to add recycled agent via flow control valve 68 and line 70 to the uppermost tray in column 18.

Still yet another alternative point at which recycled agent can be added is to condenser 22 via flow control valve 72 and flow line 74.

It is also possible, and many times desirable, to add recycled solids-preventing agent at more than one location in column 18. Any combination of points previously discussed, or others, can be employed.

In still another alternative embodiment, solids-preventing agent can be an externally added agent. For example, solids-preventing agent can be added externally via line 76 and flow control valve 78 to any of the locations previously described for recycled agent.

It should be recognized that the term "solids-preventing agent" is used herein merely as a convenience to describe the class of additives which prevent formation of solid carbon dioxide or other acid gas components in the solids potential zone. The specific mechanism by which such agents operate to prevent solids formation is not entirely understood. It may relate to increased solubility for acid gas components, but it is clear that such additives provide other advantages, some of which are described below.

In general, any material or mixture of materials which prevents acid gas solids from forming in the solids potential zone are satisfactory as solids-preventing agents. Nonpolar liquids which are miscible with methane, such as $C_3-C_6$ alkanes, are preferred agents because they are typically present in feed gases, are easy to separate and recycle, and seem to have a very beneficial effect on moving the system operating conditions away from critical conditions by raising the critical temperature and pressure of the system. Certain natural gas liquids (NGL) contain such alkanes and can often be separated from bottoms product in conventional separation equipment. Thus, these NGL or components thereof can be conveniently recycled. It is also clear that materials satisfactory for solids-preventing agent need not be pure materials.

In general, the solids-preventing agents should be liquid at the overhead temperature in the distillation column. It is desirable, of course, to have solids-preventing agents which have volatilities lower than carbon dioxide or other acid gases. The agent should also have a freezing point lower than this temperature to avoid solids formation of agent. For example, in a column operating at 600 psia and producing a relatively pure methane product, the temperature at the overhead will be about $-130°$ F., and so candidate agents should have a freezing point below this temperature. At other pressures, different overhead temperatures will be present.

In addition to the preferred materials mentioned above, there are other classes of materials which meet these requirements. For example, other hydrocarbons, such as ethane; halogenated hydrocarbons, such as fluoro-chloromethane compounds; ammonia; sulfur dioxide; etc., and mixtures thereof, are suitable. Those skilled in the art will know, or be able to ascertain using no more than routine experimentation, other suitable solids-preventing agents for use with the invention described herein.

The amount of agent added will be dependent upon factors such as the composition of the feed, operating pressure, throughput of the column, desired purity of overhead methane, etc. Such factors can be taken into account by those skilled in the art by determining the operative amounts for any given separation using no more than routine experimentation. In the case of a 50/50 methane/carbon dioxide binary feed to be separated at 600 psia, it has been calculated that amounts of n-butane used as solids-preventing agent ranging from about 0.05 moles to 0.30 moles agent per mole of feed are suitable. Since addition of the agent also sometimes increases carbon dioxide solubility, it is believed that amounts even lower than those calculated can be employed.

It has also been found, in certain cases, that better results are achieved if the total amount of agent added is distributed on more than one location within the column. This is another factor which those skilled in the art can determine using the teachings of this invention together with no more than routine experimentation.

In order to further describe this invention, a number of computer simulations will now be described. These were run using a plate-to-plate column calculation program to simulate conditions within the distillation column for certain given or desired operating conditions. The program employed was the PROCESS SM Simulation Program from Simulation Sciences, Inc., Fullerton, Calif., June–July 1979. Vapor-liquid equilibria and thermodynamic data for methane/carbon dioxide systems were calculated based upon the Soave-Redlich-Kwong equation of state.

Figure 6:
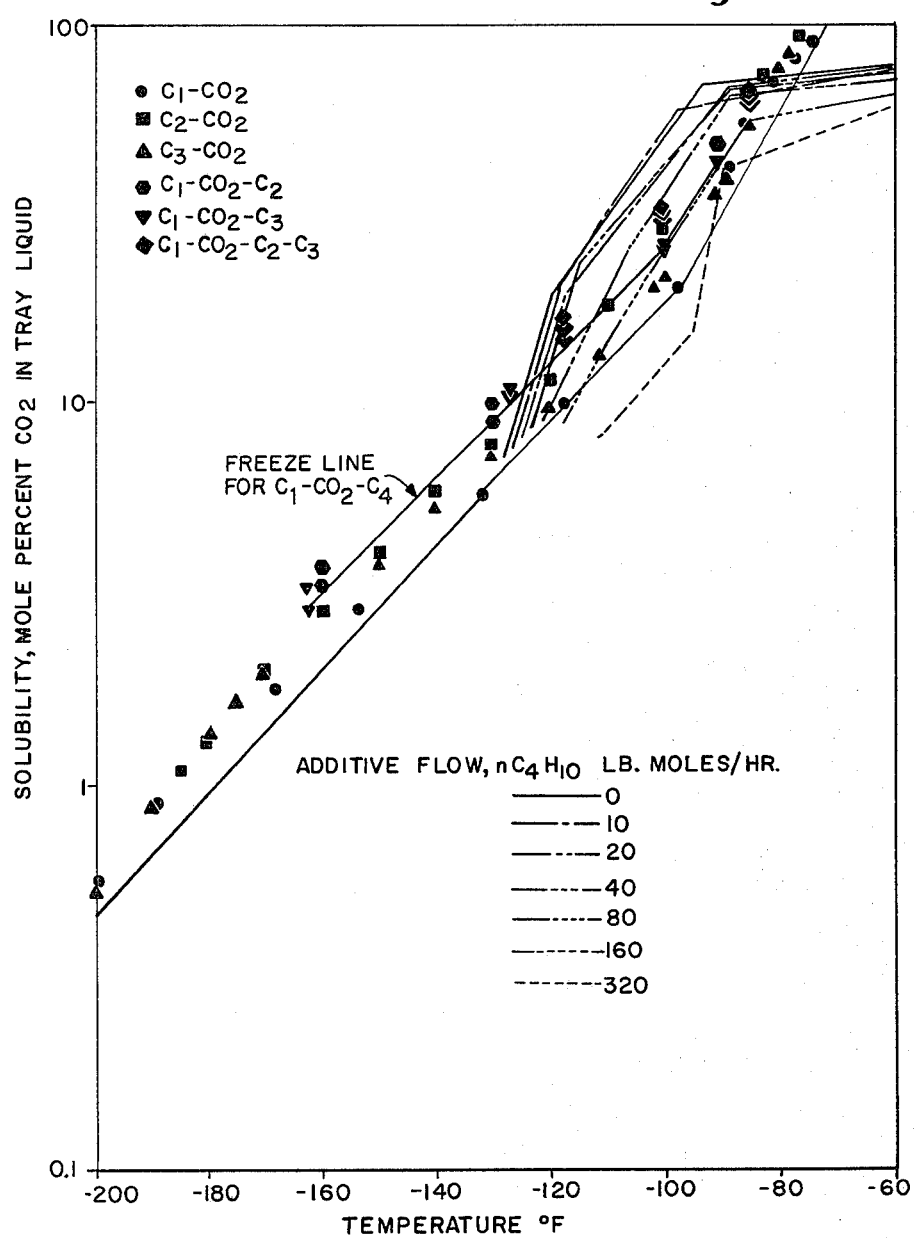

Initially, as shown in Table 1, a binary system of methane/carbon dioxide at 500 psia was chosen. However, the rigorous distillation technique could not converge for the binary system.

n-Butane was the added as a solids-preventing agent to the binary methane/carbon dioxide mixture and the conditions within the tower were calculated for 500 psia. When butane was added to the condenser, the program converged. Table 1 and FIG. 6 illustrate that when butane was added only to the condenser, the condenser temperature increased by up to about 20° F. when 320 moles per hour of butane were added. The reduced temperature (actual temperature/critical temperature) of the reflux also moved well away from criticality. Butane losses in the overhead were satisfactorily low.

system away from the solids formation zone. This increase in carbon dioxide solubility due to the presence of the agent can be seen clearly in FIG. 6, wherein the freeze line for the methane/carbon dioxide/butane systems is illustrated.

As can be seen in FIG. 6, the liquid composition moved away from the freezing region for the condenser and top two trays in the column. However, tray 2 remained in the potential freezing region as predicted by the line of lowest solubility even when 320 moles/hour

TABLE I

Binary Feed
500 psia
Reflux Ratio = 1.0

Conditions: Feed 2000 Moles/Hr., 50% $CH_4$, 50% $CO_2$
500 psia
additive at −100° F. added to condenser
additive is n-butane
Reflux ratio (moles reflux/moles overhead product) = 1.0
Overhead specification 97.5% $CH_4$, vapor product
Feed added to tray 2, 100% liquefied
5 trays in column Additive Flow Moles/Hr.

| Tray: Temp °F./% $CO_2$ in liquid | 0 | 10 | 20 | 40 | 80 | 160 | 320 |
|---|---|---|---|---|---|---|---|
| Condenser | −127.6/7.8 | −126.5/8.3 | −125.6/8.6 | −124.1/9.0 | −121.9/9.4 | −117.7/9.1 | −106.4/7.1 |
| 1 | −119.5/22.0 | −117.2/24.5 | −115.2/25.5 | −112.1/26.5 | −107.7/25.8 | −102.3/22.5 | −94.6/15.6 |
| 2 | −99.3/69.0 | −95.4/69.4 | −92.8/68.9 | −89.7/67.2 | −87.1/63.4 | −86.7/56.1 | −91.1/43.6 |
| 3 | −36.9/87.4 | −32.7/87.2 | −31.5/86.5 | −30.4/85.0 | −32.5/81.6 | −40.7/74.5 | −64.0/58.2 |
| 4 | 8.0/ | 9.6/ | 10.1/ | 10.2/ | 8.7/ | 3.0/ | −20.4/72.8 |
| 5 | 23.8/ | 24.9/ | 24.9/ | 25.3/ | 25.4/ | 24.0/ | 13.6/ |
| Reboiler | 28.9/ | 29.7/ | 30.4/ | 31.5/ | 33.3/ | 35.9/ | 36.6/ |
| Condenser duty, MMBTU/Hr. | 2.08 | 2.17 | 2.23 | 2.31 | 2.37 | 2.28 | 1.77 |
| Reboiler duty, MMBTU/Hr. | 5.94 | 6.16 | 6.35 | 6.67 | 7.14 | 7.74 | 8.32 |
| Converged? | Almost | Yes | Yes | Yes | Yes | Yes | Yes |
| Number of Iterations | 10 | 10 | 9 | 8 | 6 | 5 | 6 |
| Reduced Temp. * of Reflux | 0.925 | 0.915 | 0.905 | 0.886 | 0.852 | 0.796 | 0.716 |
| Reduced Temp. * of Bottoms | 0.894 | 0.892 | 0.889 | 0.885 | 0.876 | 0.861 | 0.835 |
| N-Butane in Overhead Moles/Hr. | 0 | 0.115 | 0.195 | 0.306 | 0.446 | 0.649 | 1.156 |
| $CH_4$ in bottoms, Moles/Hr. | 4.27 | 4.32 | 4.54 | 5.17 | 6.90 | 11.8 | 33.2 |

Reduced Temp = $\frac{\text{temp., absolute}}{\text{critical temp., absolute}}$

In FIG. 6, a solid line has been drawn to indicate the lowest solubility of carbon dioxide which was found from solubility data of carbon dioxide in the following six systems: $C_1$-$CO_2$; $C_2CO_2$; $C_3$-$CO_2$; $C_1$-$CO_2$-$C_3$; $C_1$-$CO_2$-$C_3$; and $C_1$-$CO_2$-$C_2$-$C_3$. Data for these systems were obtained from Kurata, "Solubility of Solid Carbon Dioxide in Pure Light Hydrocarbons and Mixtures of Light Hydrocarbons," Research Report 10, Gas Processors Association, (Feb., 1974).

It should be noted that addition of the hydrocarbon had the beneficial effect of increasing the carbon dioxide solubility in addition to its effect in moving the butane for 2,000 moles/hour of 50/50 methane/carbon dioxide feed was employed. It should be further noted, however, that the runs utilizing both 160 and 320 moles/hour of butane were outside the zone of freezing for a butane-containing system.

Figure 7:
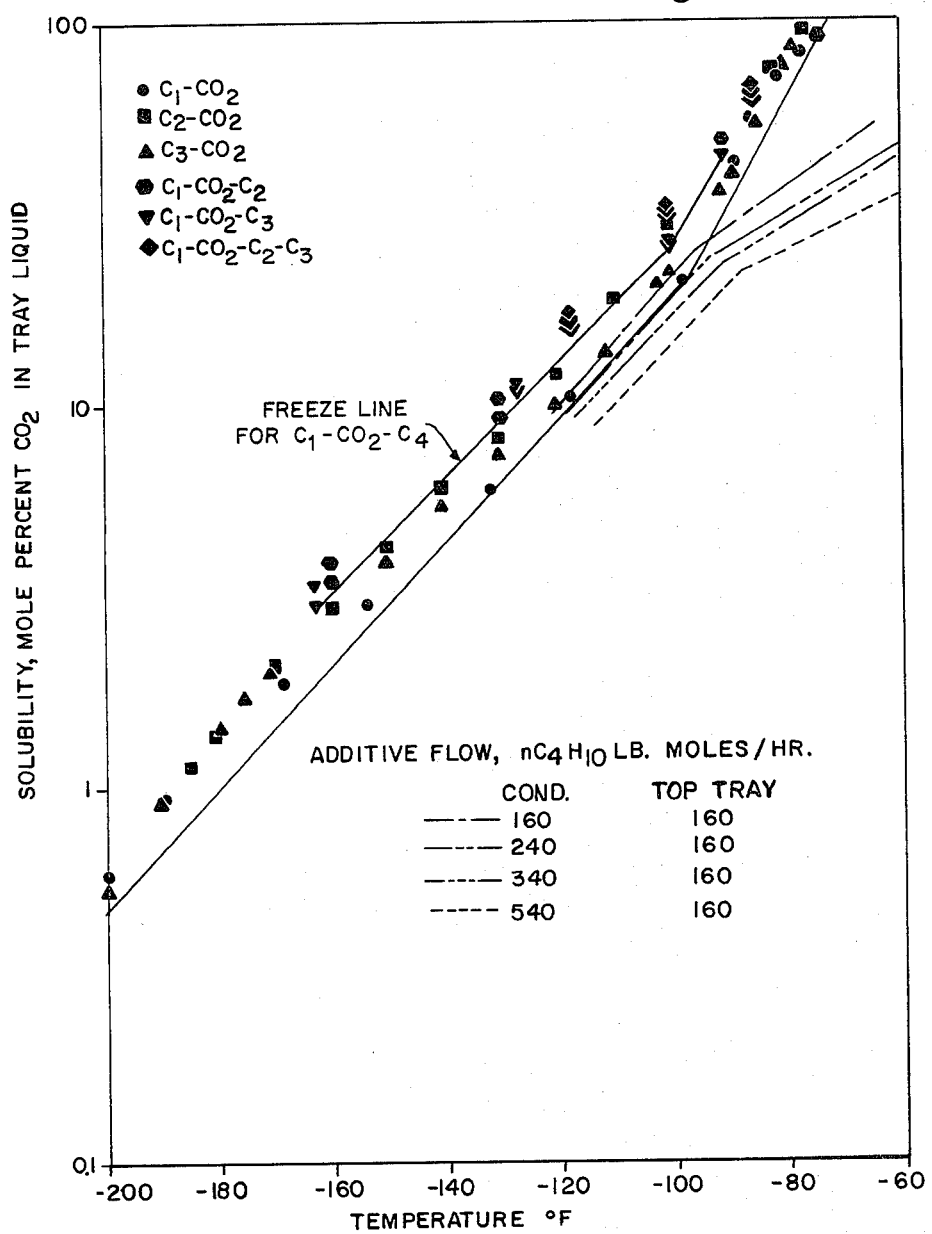

Butane was then added to the condenser and tray 1 and Table II and FIG. 7 present the results. The operating line moved significantly away from the solids region with 540 moles per hour butane added to the condenser and 160 moles per hour added to tray 1. Again, all of these cases avoid freezing when the solubility increase due to butane addition is realized.

TABLE II

Binary Feed
500 psia
More Reflux

Conditions: Feed 2000 Moles/Hr, 50% $CH_4$, 50% $CO_2$
500 psia
additive at −115° F. added to condenser and at −95° F. to tray 1
additive is n-butane
overhead specification 97.5% $CH_4$
overhead specification 1017 mols/hr.
6 trays in column
feed at −65° F. 47% liquefied, to tray 3

| | | | | |
|---|---|---|---|---|
| Additive flow to condenser, Moles/Hr | 160 | 240 | 340 | 540 |
| Additive flow to tray 1, Moles/Hr | 160 | 160 | 160 | 160 |
| Tray: Temp. °F./% $CO_2$ in liquid | | | | |
| Condenser | −121.3/9.4 | −119.5/9.3 | −117.5/9.1 | −114.4/8.6 |
| 1 | −97.0/24.5 | −94.4/23.9 | −91.9/23.1 | −88.3/21.8 |

TABLE II-continued

|  | Binary Feed 500 psia More Reflux | | | |
|---|---|---|---|---|
| 2 | −64.3/43.1 | −61.4/41.8 | −58.7/40.4 | −54.6/38.7 |
| 3 | −28.3/69.0 | −25.2/67.5 | −22.1/65.8 | −17.3/63.4 |
| 4 | 3.7/ | 6.4/ | 9.0/ | 13.1/ |
| 5 | 23.0/ | 24.9/ | 26.8/ | 29.8/ |
| 6 | 32.7/ | 34.2/ | 35.8/ | 38.5/ |
| Reboiler | 43.8/ | 46.2/ | 50.7/ | 58.4/ |
| Condenser duty, MMBTU/Hr. | 4.45 | 4.69 | 4.97 | 5.54 |
| Reboiler duty, MMBTU/Hr. | 7.22 | 8.02 | 9.01 | 11.02 |
| Converged ? | Yes | Yes | Yes | Yes |
| Number of Iterations | 7 | 7 | 7 | 8 |
| N-Butane in overhead Moles/Hr | 0.48 | 0.57 | 0.66 | 0.80 |
| % $CH_4$ in bottoms | 0.67 | 0.63 | 0.59 | 0.52 |
| Reflux Ratio | 1.76 | 1.89 | 2.08 | 2.48 |

Figure 8:
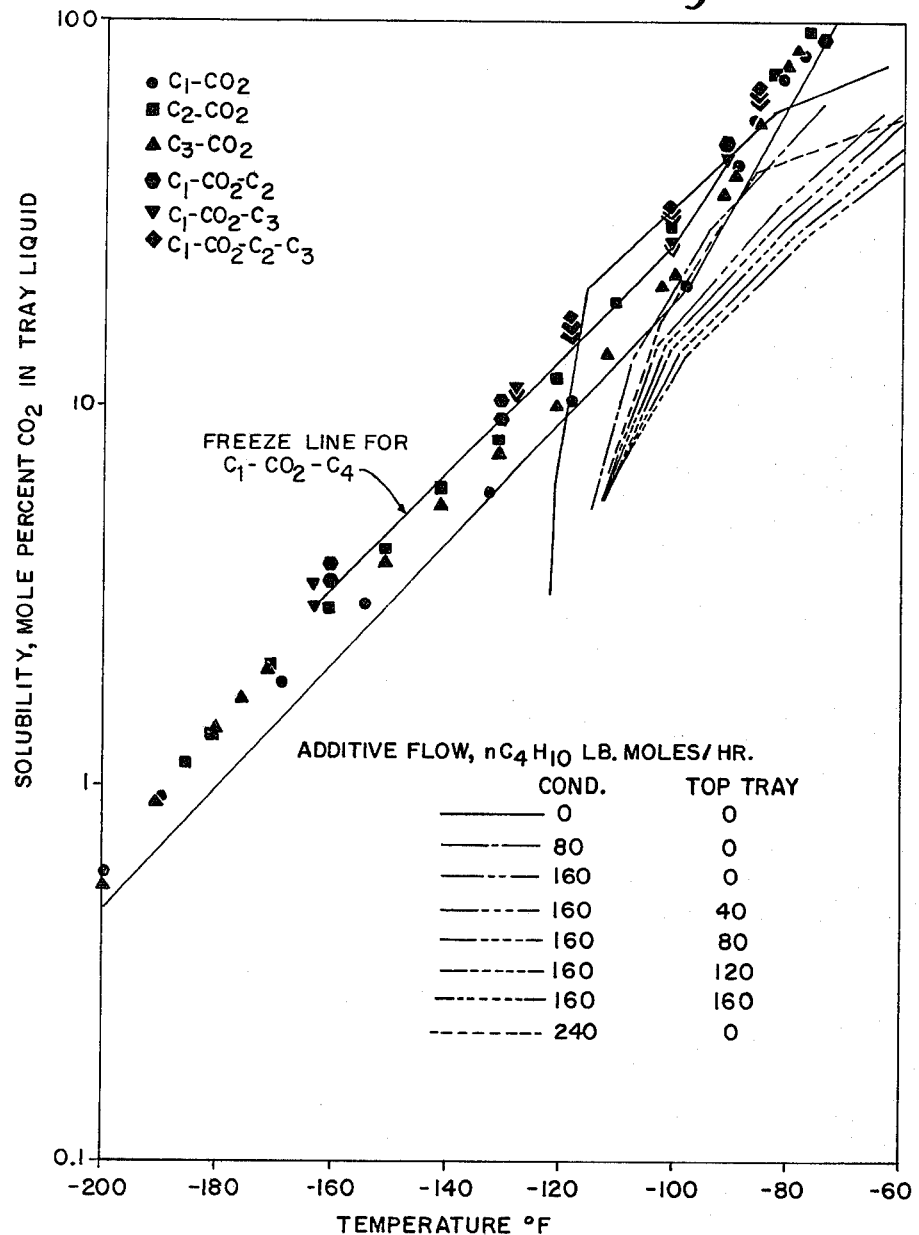

A simulation was then run for a 50/50 methane/carbon dioxide feed with butane added as solids-preventing agent at 600 psia in the tower. Table III and FIG. 8 present the data obtained. It is evident that the separation would encroach upon the solids formation zone without butane addition.

be designed for still higher pressures because of the addition of butane as a solids-preventing agent.

Further computer simulations were made changing the feed to one including nitrogen, ethane and other hydrocarbons. The specific feed chosen was as follows:

TABLE III

Binary Feed 600 psia

Conditions: Feed 2000 Moles/Hr; 50% $CO_2$, 50% $CH_4$
600 psia

Additive added at −110° F. to condenser and at −95° F. to tray 1
Additive is n-butane
Overhead specification 98% $CH_4$, vapor product
Second specification is either reflux ratio or overhead flow as underlined
Feed at −73° F. to tray as shown by underline

| | | | | | | | |
|---|---|---|---|---|---|---|---|
| Overhead flow, Moles/Hr | 1016 | 1016 | 1017 | 1017 | 1017 | 1017 | 1017 |
| Additive flow to condenser, Moles/Hr | 0 | 80 | 160 | 160 | 160 | 160 | −160 |
| Additive flow to tray 1, Moles/Hr | 0 | 0 | 0 | 40 | 80 | 120 | 160 |
| Tray: Temp, °F./% $CO_2$ in liquid | | | | | | | |
| Condenser | −122.1/3.1 | −114.8/5.2 | −112.4/5.6 | −112.5/5.6 | −112.6/5.6 | −112.7/5.6 | −112.8/5.6 |
| 1 | 121.3/4.2 | −108.4/12.8 | −103.4/14.4 | −101.9/14.2 | −100.5/14.0 | −99.2/13.8 | −98.1/13.6 |
| 2 | −120.6/6.5 | −94.0/29.2 | −85.0/30.1 | −82.7/29.4 | −80.7/28.8 | −79.0/28.2 | −77.5/27.6 |
| 3 | −119.2/9.5 | −74.9/58.4 | −62.8/58.3 | −59.8/57.3 | −57.3/56.4 | −55.2/55.6 | −53.3/54.8 |
| 4 | −117.3/13.0 | −53.0/68.9 | −34.6/69.4 | −30.4/68.6 | −27.2/67.8 | −24.6/67.1 | −22.3/66.4 |
| 5 | −115.7/21.5 | −19.2/79.2 | −1.6/79.1 | 2.1/ | 4.8/ | 7.1/ | 9.0/ |
| 6 | −82.7/57 | 11.0/ | 22.5/ | 25.5/ | 27.0/ | 28.6/ | 30.0/ |
| 7 | −62.7/ | 29.2/ | 36.1/ | 37.8/ | 39.1/ | 40.3/ | 41.3/ |
| 8 | −17.1/ | 38.6/ | 42.9/ | 44.2/ | 45.3/ | 46.2/ | 47.0/ |
| 9 | 18.1/ | 43.4/ | 46.7/ | 47.9/ | 48.9/ | 49.8/ | 50.6/ |
| 10 | 34.4/ | | | | | | |
| 11 | 39.9/ | | | | | | |
| Reboiler | 41.1/ | 47.8/ | 52.8/ | 55.0/ | 57.1/ | 59.0/ | 60.9/ |
| Trays in column | 11 | 9 | 9 | 9 | 9 | 9 | 9 |
| Condenser duty, MM BTU/Hr | 2.69 | 2.98 | 3.20 | 3.37 | 3.52 | 3.67 | 3.81 |
| Reboiler duty, MM BTU/Hr | 4.28 | 5.34 | 6.31 | 6.78 | 7.22 | 7.65 | 8.07 |
| Coverged ? | No | Yes | Yes | Yes | Yes | Yes | Yes |
| Number of Iterations | 10 | 6 | 6 | 7 | 6 | 6 | 6 |
| Reduced Temp of reflux | 0.966 | 0.923 | 0.881 | 0.883 | 0.885 | 0.887 | 0.888 |
| Reduced Temp of Bottoms | 0.922 | 0.901 | 0.888 | 0.882 | 0.877 | 0.872 | 0.867 |
| N-Butane in OH, Moles/Hr | 0 | 0.865 | 1.083 | 1.074 | 1.066 | 1.059 | 1.053 |
| % $CH_4$ in bottoms | 2.1 | 0.40 | 0.32 | 0.31 | 0.30 | 0.29 | 0.28 |
| Reflux Ratio | 1.70 | 1.70 | 1.70 | 1.75 | 1.79 | 1.84 | 1.88 |

Due to the higher pressures, temperatures were higher and substantially less solids-preventing agent was needed. One hundred sixty moles per hour added to both the condenser and tray 1 moved the operating line out of the solids potential zone.

The liquid reduced temperature in the condenser came down to 0.888, indicating that the process could

| Component | Mole % |
|---|---|
| $N_2$ | 4.85 |
| $CO_2$ | 50.00 |
| $H_2S$ | .15 |
| $CH_4$ | 25.67 |
| $C_2H_6$ | 7.93 |
| $C_3H_8$ | 6.62 |

-continued

| Component | Mole % |
|---|---|
| $C_4H_{10}$ | 3.20 |
| $C_5H_{12}$ | 1.26 |
| $C_6H_{14}$ | .23 |
| $C_7H_{16}$ | .09 |
| $H_2O$ | <1 PPM |
| Total | 100.00 |

Figure 9:
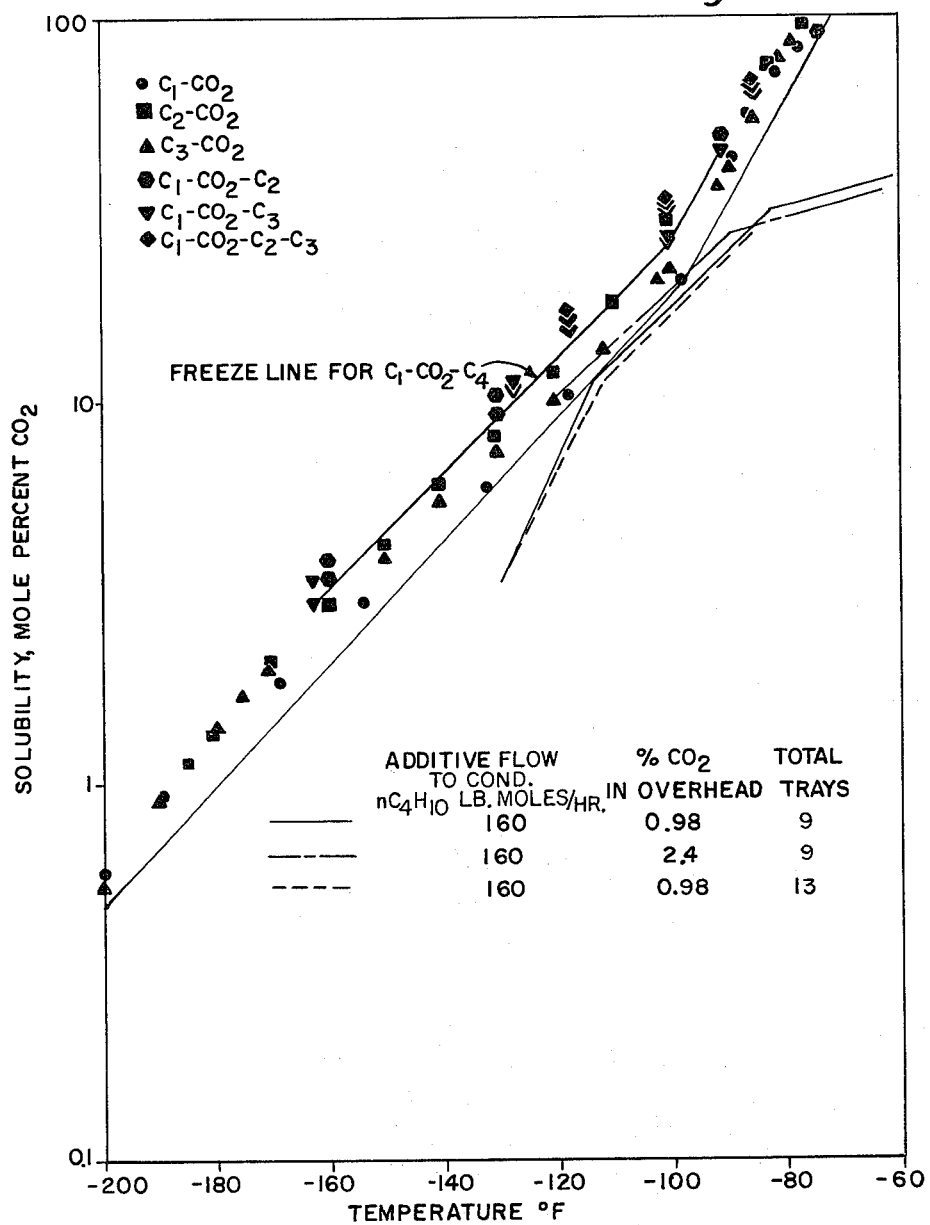

The results are presented in Table IV and FIG. 9. As can be seen, the operating line was once again moved out of the solids formation zone, which itself was moved further to the left. Thus, lower amounts of agent can be employed than these amounts calculated without taking into account the increase in carbon dioxide solubility due to the presence of the agent.

TABLE IV

Multicomponent Feed
600 psia

Conditions: Feed 2000 Moles/Hr - includes $N_2$ and ethane-plus, per text
600 psia
Additive at $-110°$ F. added to condenser
Overhead Specification 0.98% $CO_2$
Bottoms Specification 0.32% $CH_4$
Feed at $-51°$ F. to tray as shown, 85% liquefied

| | | | | |
|---|---|---|---|---|
| Additive flow to condenser, Moles/Hr | 160 | 160 | 160 | 160 |
| Tray: Temp, °F./% $CO_2$ in liquid | | | | |
| Condenser | −130.2/3.5 | −122.4/9.7 | −127.8/3.8 | −127.6/3.8 |
| 1 | −114.4/11.2 | −88.6/27.7 | −111.7/11.5 | −112.3/11.6 |
| 2 | −83.1/30.5 | −43.8/43.5 | −85.9/ | −88.4/27.7 |
| 3 | −37.2/51.0 | −16.3/56.1 | −30.5/43.1 | −55.8/43.0 |
| 4 | −6.7/58.9 | 7.1/ | −22.7/53.7 | −33.7/50.5 |
| 5 | 15.9/ | 23.1/ | −5.2/57.6 | −23.5/52.8 |
| 6 | 29.7/ | 33.0/ | −9.9/61.4 | −19.3 |
| 7 | 37.3/ | 38.9/ | 22.0/ | −17.6/ |
| 8 | 41.5/ | 42.3/ | 30.8/ | −16.8/ |
| 9 | 44.5/ | 44.9/ | 36.8/ | −17.2/ |
| Total Trays/Feed Tray | 9/2 | 9/2 | 13/5 | 18/10 |
| Condenser duty, MM BTU/Hr | 5.93 | 4.26 | 2.80 | 2.61 |
| Reboiler duty, MM BTU/Hr | 9.62 | 8.06 | 6.530 | 6.34 |
| Converged? | Yes | Yes | Yes | Yes |
| Number of Iterations | 8 | 7 | 14 | 9 |
| Reduced Temp of Reflux | 0.901 | 0.844 | 0.843 | 0.837 |
| Reduced Temp. of Bottoms | 0.897 | 0.896 | 0.897 | 0.897 |
| N-Butane in Overhead Moles/Hr | 0.28 | 0.35 | 0.36 | 0.37 |
| % $CO_2$ in overhead | 0.98 | 2.4 | 0.98 | 0.98 |
| % $CH_4$ in bottoms | 0.32 | 0.32 | 0.32 | 0.32 |
| Reflux Ratio | 5.22 | 2.83 | 2.33 | |

Although most of the description of specific processes given above has been done in terms of carbon dioxide, it is believed that other acid gas components, such as hydrogen sulfide, carbonyl sulfide, etc., would act similarly. This is corroborated by the teachings of the prior art. See, for example, Chueng, H. and Zander, E. H., CEP Symposium Series 88, Vol. 64 (1968); and Eakman et al., U.S. Pat. No. 4,149,864.

Industrial Applicability

This invention is useful in the cryogenic distillative separation of methane from mixtures containing methane and relatively high amounts of carbon dioxide and/or other acid gas components, as well as in other cryogenic distillative separations, such as the separation of methane from ethane.

Equivalents

Those skilled in the art will also recognize, or be able to determine using no more than routine experimentation, other equivalents to the specific embodiments described herein. For example, although most of the description herein has been related to relatively high pressure systems, e.g., 500 psia, it is clear that the invention operates with much lower pressure systems. Additionally, the description above was related to the desired to remove acid gas components from the distillation tower, but the invention applies in systems where $CO_2$ or other acid gas components, or portions thereof, may be left in the tower, such as separations of methane from ethane. These and other equivalents are intended to be covered by the claims appended hereto.

It also should be recognized, of course, that specific numbers given with regard to carbon dioxide will change for other acid gas components. For example, whereas 3% carbon dioxide might be tolerable in the overhead product, this amount of hydrogen sulfide would normally be intolerable.

We claim:

1. In a method for the distillative cryogenic separation of a mixture containing methane and an acid gas component in a distillation column to separate an enriched methane overhead product and a bottoms product containing a major portion of the acid gas component, and wherein said column is operated under conditions of temperature, pressure and acid gas composition which create a solids potential zone in the upper portion of said column, where said acid gas component would normally form solids:

the improvement which comprises adding a liquid solids-preventing agent for said acid gas component to the solids potential zone at a point in said column in an amount sufficient to be present substantially throughout the solids potential zone in sufficient quantity, to prevent acid gas solids from occurring in the solids potential zone, and withdrawing the liquid agent with the acid gas containing bottoms product.

2. The improvement of claim 1 wherein said solids-preventing agent comprises a nonpolar liquid which is miscible with methane at the column conditions.

3. The improvement of claim 1 wherein said solids-preventing agent comprises natural gas liquids.

4. The improvement of claim 1 wherein said solids-preventing agent comprises ethane, propane, butane, pentane or mixtures thereof.

5. The improvement of claims 1, 2, 3 or 4 wherein said solids-preventing agent is separated from bottoms product and recycled to said column.

6. The improvement of claim 5 wherein said acid gas component comprises carbon dioxide.

7. The improvement of claim 6 wherein substantially all of said carbon dioxide in the gas mixture is removed from the overhead methane product.

8. The improvement of claim 6 wherein said solids-preventing agent is introduced into said distillation column at a plurality of locations.

9. The improvement of claim 4 wherein said acid gas component comprises hydrogen sulfide.

10. The improvement of claim 9 wherein substantially all of said hydrogen sulfide in the gas mixture is removed from the overhead methane product.

11. A method for separating methane from a mixture containing methane and an acid gas, comprising:
   (a) introducing said mixture into a distillation column containing a plurality of vapor-liquid contact devices;
   (b) operating said distillation column at conditions of pressure, temperature and acid gas composition sufficient to separate an enriched methane overhead product and a bottoms product containing a major portion of the acid gas, said conditions of temperature, pressure and acid gas composition creating a solids potential zone for acid gas components within said distillation column, where said acid gas components would normally form solids;
   (c) introducing a liquid solids-preventing agent into the solids potential zone in the upper portion of said column in sufficient amount to eliminate acid gas solids formation in the solids potential zone; and
   (d) withdrawing the liquid-solids-preventing agent with the acid gas containing bottoms product.

12. A method of claim 11 wherein said solids-preventing agent comprises a nonpolar liquid which is miscible with methane at the column conditions.

13. A method of claim 12 wherein said solids-preventing agent is separated from bottoms product and recycled to the column.

14. A method of claim 12 wherein said solids-preventing agent is introduced into said distillation column at a plurality of locations.

15. A method of claims 11, 12, 13 or 14 wherein said acid gas comprises carbon dioxide.

16. A method of claims 11, 12, 13 or 14 wherein said acid gas comprises hydrogen sulfide.

17. A method of separating methane from a feed stream containing methane and carbon dioxide, comprising:
   (a) cooling said feed stream;
   (b) introducing said cooled feed stream into a distillation column having a plurality of vapor-liquid contact stages, said column being maintained under conditions of pressure, temperature and acid gas compositions which create a solids potential zone therein;
   (c) providing sufficient heat at the bottom of said column to provide an enriched methane overhead stream;
   (d) condensing a portion of said methane overhead stream by cooling it and directing it back to the top of said column as a reflux;
   (e) withdrawing a methane overhead stream as product;
   (f) withdrawing a bottoms product stream containing a major portion of the carbon dioxide from the bottom of said column;
   (g) introducing liquid, solids-preventing agent into said solids potential zone of the distillation column in an amount sufficient to be present substantially throughout the solids potential zone and in a sufficient quantity to prevent acid gas solids formation therein; and withdrawing the liquid agent with the bottoms product stream containing carbon dioxide from the bottom of the column.

18. A method of claim 17 wherein said solids-preventing agent comprises a nonpolar liquid which is miscible with methane at column conditions.

19. A method of claim 17 wherein said solids-preventing agent comprises one or more $C_2$–$C_5$ alkanes.

20. A method of claims 17, 18 or 19 wherein said solids-preventing agent comprises an agent separated from bottoms product and recycled to said column.

* * * * *